| United States Patent [19] | [11] Patent Number: 5,026,944 |
| --- | --- |
| Allenger et al. | [45] Date of Patent: Jun. 25, 1991 |

[54] SYNTHESIS OF ISOBUTENE FROM METHANE AND ACETYLENE

[75] Inventors: Vincenza Allenger, Kanata; Raj N. Pandey, Guelph, both of Canada; Prasad Yarlagadda, Amherst, N.Y.

[73] Assignee: Energy Mines and Resources Canada, Ottawa, Canada

[21] Appl. No.: 453,937

[22] Filed: Dec. 20, 1989

[51] Int. Cl.$^5$ .......................... C07C 2/00; C07C 2/56
[52] U.S. Cl. .................... 585/500; 585/700; 585/709
[58] Field of Search ...................... 585/500, 700, 709

[56] References Cited

U.S. PATENT DOCUMENTS

| 4,433,192 | 2/1984 | Olah | 585/627 |
| 4,465,893 | 8/1984 | Olah | 585/709 |
| 4,467,130 | 8/1984 | Olah | 585/709 |
| 4,513,164 | 4/1985 | Olah | 585/700 |

Primary Examiner—H. M. S. Sneed
Assistant Examiner—James Saba

[57] ABSTRACT

A process is described in which methane is reacted with acetylene in the presence of a solid acid catalyst containing fluoride to produce isobutene in high yields. The process may take place at room temperature or lower and atmospheric pressure. The conversion of acetylene typically approaches 100% and the methane conversion has been found to surpass stoichiometric requirements.

7 Claims, No Drawings

SYNTHESIS OF ISOBUTENE FROM METHANE AND ACETYLENE

BACKGROUND OF THE INVENTION

This invention relates to the direct conversion of methane and acetylene into isobutene.

Isobutene is typically recovered as a product from refinery light-end operations by conventional methods. The isobutene is used primarily as a reactant together with formaldehyde to synthesize isoprene. Isobutene may also be reacted with methanol to produce methyl tertiary butyl ether (MTBE). Other possible uses for isobutene include hydration to gasoline grade tertiary butyl alcohol, alkylation with $C_4$ olefins to make alkylation gasoline, polymerization to diesel fuel, jet fuel and polymer gasoline and as an RBP blending component.

Demands for isobutene are expected to increase dramatically and this has necessitated exploring new synthesis routes for the alkene. However, new sources of isobutene have been limited to dehydrogenation of isobutane from field butanes.

The reaction of methane with acetylene under mild conditions in the presence of Fe(acetylacetonate)$_3$-Et$_3$Al catalyst has been reported to lead to the formation of propylene with complete suppression of the self-polymerization of acetylene (Grigoryan, E.A. et al. Dokl. Akad. Nauk SSSR, 257, 364, 1981). The formation of propylene is believed to occur via insertion of acetylene at a Fe-CH$_3$ bond and subsequent elimination of a metal hydride complex of Fe.

The reaction between methane and acetylene to $C_4$ hydrocarbons is thermodynamically favorable over a range of temperatures as shown by the free energy calculations in the following table:

Free energy for some possible reactions

| Reaction | ΔG (kcal/mol) | | |
|---|---|---|---|
| | 300 K | 400 K | 500 K |
| 1. $2CH_4 + C_2H_2 \rightarrow C_4H_8 + H_2$ | −9 | −5 | −2 |
| 2. $2CH_4 + C_2H_2 \rightarrow C_4H_{10}$ | −30 | −24 | −17 |
| 3. $2C_2H_2 + 3H_2 \rightarrow C_4H_{10}$ | −104 | −92 | −80 |
| 4. $4CH_4 \rightarrow C_4H_{10} + 3H_2$ | 44 | 45 | 46 |

$\Delta G_{rxn} = \Delta G_{pro} - \Delta G_{rea}$

Alkylations such as that of isobutane with isobutene or any other $C_4$ olefin to produce $C_8$ alkylate are well known in the petrochemical industry. These alkylations are acid catalyzed and the catalysts employed are HF and $H_2SO_4$. Until recently, the alkylation of the lower alkanes with alkenes has been studied in liquid acid media and liquid phase reaction conditions were considered to substantially limit practical application of the reaction. In addition, the products were a mixture of oily oligomers whose molecular weight ranged from 100 to 700.

The alkylation of methane and olefins (alkynes) has received special attention since it was reported in Olah, U.S. Pat. No. 4,465,893, issued Aug. 14, 1984, that alkylation between methane and ethylene could be conducted over a solid superacid catalyst.

It is the object of the present invention to find a simple method for producing isobutene starting from methane or natural gas as a reactant.

SUMMARY OF THE INVENTION

According to the present invention, a practical way has been found to directly convert methane and acetylene into isobutene by reacting a gaseous feed comprising methane or natural gas and acetylene in the presence of a solid or supported superacid catalyst.

The methane is readily available from natural gas, which typically contains from about 40 to about 95 volume % methane. Acetylene may be derived by the pyrrolysis of natural gas and coal or the reaction of calcium carbide with water.

Catalysts of the general type described in U.S. Pat. No. 4,465,893 are suitable for use in the process of this invention and these are typically solid superacid halides of metals of groups IV, V or VI of the Periodic Table, supported on carrier. They are preferably in the form of fluorides with binary metal fluoride catalysts being particularly useful, e.g. those of antimony, niobium and tantalum. Among specific preferred catalysts, there may be mentioned tantalum pentafluoride, antimony pentafluoride and niobium pentafluoride. Typical carriers for the binary catalyst may include anhydrous aluminum trifluoride, fluoridated alumina, graphite, fluoridated graphite and non-exchange supports, e.g. aluminosilicates.

The process may be carried out at low temperatures of even below 0° C. and generally below 150° C., with a range of about 20°–50° C. being highly satisfactory. Low pressures in the range of 1 to 25 atmospheres may also be used with a range of 5 to 10 atmospheres being preferred. The feedstock preferably comprises a mixture of methane and acetylene in mol. ratios of 1–10:1 of methane to acetylene. These reactions generally produce isobutene with a high selectivity in the order of 95 mol. %, the remaining 5 mol. % typically comprising n-butane, 1-butene, ethane and propane. At the end of the cycle, the catalyst may be easily regenerated.

Although the process described herein uses a fixed catalyst bed, other well known techniques may be used, e.g. a fluidized bed, for contacting the gaseous feed with the catalysts.

Illustrative of the invention are the following examples, set forth for the purpose of illustration only and not to be construed as limiting the scope of the invention in any manner. In the related tables where product tables are given, they have been normalized, even if not stated, to provide a total of 100% conversion, excluding unreacted methane and acetylene which can be recycled.

EXAMPLE 1

A methane:acetylene feed (about 95:5 mol. ratio) containing nitrogen for analytical purposes was reacted over a series of different binary fluoride catalysts (50 wt % mixture) in a fixed bed continuous flow reactor at a temperature of 25° C., a pressure of 10 atm and a GHSV of 150.

The binary catalysts consisted of 50 wt % of TaF$_5$, NbF$_5$ or SbF$_5$ as catalyst and 50 wt % of AlF$_3$ or CF$_{0.6}$ as support.

Catalysts with AlF$_3$ support

To prepare a SbF$_5$-AlF$_3$ catalyst, 5 grams of SbF$_5$ was dissolved in 125 ml of anhydrous HF in a flask fitted with a stirrer and an exhaust. With the flask at a temperature of about 0° C., 5 grams of AlF$_3$ was added to the solution in the flask and stirred for 1 hour. There-after, the temperature of the flask was raised to evaporate any excess HF to dryness, after which the mixture was held at 100° C. for 6 hours. The above procedure was repeated with 5 grams of each of $TaF_5$ and $NbF_5$.

Catalysts with Fluorinated Graphite support

To prepare a $TaF_5$—$CF_{0.6}$ catalyst, 5 grams of fluorinated graphite was dried for 12 hours at 100° C. Then it was transferred into a 500 ml reaction flask fitted with a condenser, stirrer and a nitrogen gas inlet. 5 Grams of $TaF_5$ dissolved in 125 ml of 1,1,2-trichlorotrifluoroethane was added to the above flask with stirring and the temperature in the flask was maintained at about 45° C. Refluxing was continued for 6 hours, after which the solvent was evacuated and the mixture was heated with occassional stirring at 100° C. for 12 hours. The above procedure was repeated with 5 grams of $NbF_5$.

To prepare a $SbF_5$ based catalyst, 5 grams of fluorinated graphite together with 5 grams of $SbF_5$ was thoroughly mixed in an atmosphere of $N_2$ at 70° C. for 6 hours.

The conversion and selectivity data are given in Table 1 below:

TABLE I

Conversion and selectivity data over the screen catalysts

| Catalyst | Conversion, mol % | | Selectivity, wt % | | | | |
|---|---|---|---|---|---|---|---|
| | $CH_4$ | $C_2H_2$ | $C_2H_6$ | $C_3H_8$ | $C_4H_{10}$ iso | n | i-$C_4H_8$ |
| $TaF_5$—$AlF_3$ | 9.9 | 100 | 6.1 | 1.0 | 3.3 | 0.2 | 89.4 |
| $NbF_5$—$AlF_3$ | 16.0 | 100 | 2.0 | 0.6 | 2.6 | 0.2 | 94.6 |
| $SbF_5$—$AlF_3$ | 21.6 | 82 | 12.5 | 2.5 | 2.4 | 6.2 | 76.8 |
| $TaF_5$—$CF_{0.6}$ | 9.5 | 100 | 5.5 | 0.5 | 3.5 | 5.9 | 84.6 |
| $NbF_5$—$CF_{0.6}$ | 10.9 | 100 | 5.3 | 2.4 | 4.1 | 7.0 | 81.2 |
| $SbF_5$—$CF_{0.6}$ | 9.0 | 100 | 4.4 | 0.5 | 5.1 | 4.4 | 85.6 |

Run time and analysis time = 30 min.

EXAMPLE 2

The variation in the conversion and selectivity with time on stream was investigated over a $NbF_5$—$AlF_3$ catalyst prepared as in Example I for a feed gas of the same composition as in Example 1. The results are summarized in Table II below:

TABLE II

Variation in conversion and selectivity with time on stream

| Time on stream [h] | Conversion, mol % | | Selectivity, wt % | | | | |
|---|---|---|---|---|---|---|---|
| | $CH_4$ | $C_2H_2$ | $C_2H_6$ | $C_3H_8$ | $C_4H_{10}$ iso | n | i-$C_4H_8$ |
| initial | 23.1 | 100 | 5.1 | 1.2 | 15.6 | 0.4 | 78.1 |
| 1 | 29.2 | 100 | 3.6 | 0.4 | 2.5 | — | 93.5 |
| 2 | 27.4 | 100 | 3.9 | 0.1 | 1.1 | — | 94.9 |
| 3 | 22.9 | 92.2 | 3.8 | 0.1 | 1.1 | — | 95.0 |
| 4 | 23.3 | 95.5 | 2.8 | 0.2 | 0.5 | — | 96.5 |

TABLE II-continued

Variation in conversion and selectivity with time on stream

| Time on stream [h] | Conversion, mol % | | Selectivity, wt % | | | | |
|---|---|---|---|---|---|---|---|
| | $CH_4$ | $C_2H_2$ | $C_2H_6$ | $C_3H_8$ | $C_4H_{10}$ iso | n | i-$C_4H_8$ |
| 5 | 12.2 | 70 | 2.6 | 0.8 | 0.2 | — | 96.4 |

— not detected

EXAMPLE 3

An acetylene-nitrogen feed gas mixture was contacted with five different catalysts in a continuous flow fixed bed reactor to determine the extent of the self-oligomerization under conditions similar to those used in Example 1. The catalysts were prepared in the same manner as in Example 1. A summary of the self-oligomerization reaction on these catalysts is given in Table II below:

TABLE III

Conversion and selectivity date over the catatlyts with acetylene in nitrogen feed

| Catalyst | Conversion, mol % | | Selectivity, wt% | | | | |
|---|---|---|---|---|---|---|---|
| | $C_2H_2$ | $CH_4$ | $C_2H_6$ | $C_3H_8$ | $C_4H_{10}$ iso | n | i-$C_4H_8$ |
| $TaF_5$—$AlF_3$ | 100 | 0.1 | 0.9 | — | — | 99.0 | — |
| $NbF_5$—$AlF_3$ | 100 | 0.4 | 0.6 | 2.7 | 12.1 | 82.6 | 1.6 |
| $TaF_5$—$CF_{0.6}$ | 100 | 2.2 | — | 0.5 | 1.5 | 95.8 | — |
| $NbF_5$—$CF_{0.6}$ | 100 | 0.9 | 0.1 | 1.1 | 9.1 | 9.1 | — |
| $SbF_5$—$CF_{0.6}$ | 100 | — | 12.9 | — | 3.1 | 3.1 | — |

The self-oligomerization of acetylene leads to severe deactivation within a short period of time and as shown in the table produces a different product (n-butane) from that of the reaction of the present invention.

We claim:

1. A gas-phase process for producing isobutene which comprises contacting methane with acetylene in the presence of a solid superacid catalyst at a temperature below 50° C.

2. A process according to claim 1 wherein the catalyst is a solid superacid halide of metals of groups IV, V or VI of the Periodic Table, supported on a carrier.

3. A process according to claim 2 wherein the halide is a fluoride.

4. A process according to claim 3 wherein the catalyst is a binary metal fluoride catalyst.

5. A process according to claim 4 wherein the catalyst is selected from tantalum pentafluoride, antimony pentafluoride and niobium pentafluoride.

6. A process according to claim 5 wherein the carrier is selected from anhydrous aluminum trifluoride, fluoridated alumina, graphite, fluoridated graphite and aluminosilicates.

7. A process according to claim 1 wherein the methane and acetylene are contacted at a pressure of about 1 to 25 atmospheres and a methane:acetylene ratio of 1–10:1.

* * * * *